United States Patent [19]

Haker

[11] 3,947,963
[45] Apr. 6, 1976

[54] ARTIFICIAL TEETH AND METHOD OF MANUFACTURING A DENTURE

[75] Inventor: Gerd Haker, Hamburg, Germany

[73] Assignee: Vita Zahnfabrik H. Rauter KG, Sackingen, Germany

[22] Filed: Mar. 31, 1975

[21] Appl. No.: 565,575

[30] Foreign Application Priority Data
May 29, 1974 Germany............................ 2426190
Apr. 6, 1974 Germany..................... 7412130[U]

[52] U.S. Cl. .................................. 32/2; 32/8; 32/12
[51] Int. Cl.² ......................................... A61C 13/00
[58] Field of Search ........................ 32/2, 3, 4, 8, 12

[56] References Cited
UNITED STATES PATENTS

| | | | |
|---|---|---|---|
| 2,230,164 | 1/1941 | Myerson | 32/8 X |
| 2,431,086 | 11/1947 | Saffir | 32/8 |
| 2,473,515 | 6/1949 | Egger | 32/8 |
| 2,744,326 | 5/1956 | Chaiken et al. | 32/12 |
| 3,273,242 | 9/1966 | Andrew | 32/12 |

Primary Examiner—Louis G. Mancene
Assistant Examiner—Jack Q. Lever
Attorney, Agent, or Firm—Diller, Brown, Ramik & Wight

[57] ABSTRACT

This disclosure is directed to a method of manufacturing an artificial denture, such as a molar or molars having cusps and occlusal relief therebetween by providing a base surface which is generally planar and flat, providing cones each having a base and apex, securing the base of each cone upon the base surface, and covering the cones with dental material such that cusps are formed by the apices of the cones and occlusal relief is formed between the apices.

10 Claims, 9 Drawing Figures

ARTIFICIAL TEETH AND METHOD OF MANUFACTURING A DENTURE

The present invention is directed to a novel method of and apparatus for manufacturing functionally formed artificial molar teeth or groups of molar teeth from ceramic or like dental material by crowning or bridgework.

Porcelain or dental ceramics has recently been proved to be of extraordinary advantage for the reconstruction and replacement of molar teeth. These materials have proved their value over many decades for replacement crowns for incisor and canine teeth as, for example, in the form of known jacket crowns. The development of the burning-on technique in which the ceramic mass is burned onto a thin crown, bridge or frame enables replacement crowns to be applied to normally prepared living teeth which fully meet desired requirements of mechanical strength. Compared with most frequently used gold crowns and gold molar surfaces, the ceramic molar surfaces in terms of anatomical shape, attractiveness and aesthetic effect of the entire set of teeth having advantages which cannot be achieved with any other material.

The chewing surfaces of the side teeth in the upper and lower jaw of an individual patient having the full number of teeth are surfaced such that the fine protuberances (cusps) and recesses (occlusal relief) fit exactly into one another. This functionally adapted occlusal field, which is coordinated in shape, results because the surface of each tooth and the position of each tooth in the dental arch are generally symmetrically arranged relative to three planes and to the axis of motion of the jaw joints. In a normal undisturbed occlusal field, this harmonized contact situation between the vertical points of contact of the teeth is found not only in the closed bite of the central occlusion, but also in fine occlusion patterns when the lower jaw is moved while the teeth are in contact resulting in a sliding on the working side of the teeth in precisely defined paths as the teeth come out of contact with each other on the passive side.

This harmony in the contact between the occlusion patterns of the upper and lower molars cause disturbances in the occlusion which can lead to damage of the tooth-retaining tissue (paradontia) and other tissue parts. Therefore, in each reformative treatment, it is important that a harmoniously-formed disturbance-free occlusal field be introduced into a patient's damaged chewing system. For this purpose, it is known to use articulators which simply are conventional apparatus in which jaw models can be moved in almost the same fashion as the teeth in the jaw of a patient.

In accordance with a conventional modeling technique a form is produced from a wax blank, and following a build-up technique, the individual occlusal patterns are built up layer by layer with continuous monitoring of the movement to achieve optimum bite. However, these methods are generally only suitable for metal or gold surfaces.

An object of the present invention is to enable the manufacturer of molar teeth or groups of molar teeth, both for crowns and bridgework, in which the molar teeth or groups of molar teeth can be rapidly, safely and precisely formed from ceramic material and with all occlusal patterns being in exacting contact with one another without disturbance.

According to the present invention a replacement crown or bridge frame is provided with a planar, flat base surface and a plurality of basic cones preformed from ceramic material are adhered to the base surface or burned onto it and the molar tooth occlusal relief is produced on this framework by applying ceramic material upon the integral base cones such that the apices of the cones form the protuberances or cusps of the molars and the areas therebetween form the molar tooth occlusal relief.

The present invention is based upon the recognition that the anatomical tooth crowns of molars can be preconstructed in a simplified way simply by constructing as each cusp or protuberance a framework or support element in the form of a cone. The round cone base, by appropriately being located upon a base surface, defines the position of the protuberance or cusp while the steepness can be varied, along with the depths of its indentations, by changes in the length of the basic cone. The basic cones can, however, be used and inserted independently as need be to obtain accurate position of the cusps of the molar and since the preformed basic cones are no longer exposed to conventional shrinkage, the shrinkage of the ceramic coating material, which is particularly intensive in the region of the cusps or protuberances is virtually eliminated, and the molar is produced virtually without shrinkage, once again because of the use of independent basic cones. This enables ceramic chewing surfaces to be produced more rapidly and with a better fit in relation to existing complimentary teeth and the frequently boring task of grinding is reduced to a minimum with the aesthetic effect being visibly improved.

With the assistance of the pre-formed porcelain base or basic cones, heretofore described, a uniform occlusal shape can be simply achieved over the entire dental arch with the occlusal form being functionally adapted to the central occlusion and each phase of movement of the lower jaw during tooth contact. As a result of the use of the pre-formed porcelain base cones, an occlusal framework is rapidly and simply set up in which all relief parts, central tops and their analogous contact areas occlude, and uniformly and simultaneously articulate in the closed bite, and also in the controlled movements of the lower jaw. It is therefore no longer necessary for occlusal chewing surfaces to be freely modeled. Thus, with the assistance of the pre-formed porcelain base cones applied to a bridge or crown and bridge framework, a technically and functionally clearly defined occlusal pattern is rapidly and reliably produced.

In setting up rows of teeth, the same functional relief parts of the individual teeth are advantageously built up by means of the prefabricated or pre-formed basic cone which fits with these into the pre-existing occlusal framework of a patient and blends readily therewith.

Clinical experience has shown that certain special features can occur in individual chewing systems which have to be taken into account, along with other features such as vertical spacing (bite height) and steepness of the joint track. It is therefore appropriate to have the base or basic cones formed as prefabricated parts in several sizes which can be standardized as, for example, high, medium and short. Generally, these three standard sizes of height will be sufficient for all purposes. Since the cone surfaces are the same, as measured on the medial molar cross-section, the three standard cone heights would give rise to three cone track angles and in this way a corresponding modification can be obtained by modeling the interspaces between the cones.

In special circumstances as, for example, raising the bite of a person, reconstruction of the bite position, or for particularly small preparative inter-occlusal slots, special sizes of the prefabricated base cones can be prepared with the bases thereof differing additionally by smaller and larger cross-sectional areas. The base areas of the cones are advantageously about 3mm (± 1 mm for special shapes), so that occlusal relief results strictly from covering the cones themselves with ceramic material. The base cones can, of course, be shifted horizontally within a tolerance range upon the base surface, be it a bridge or like framework, to enable an individual-functional adaptation to the geometric values of a person's individual chewing system.

With the above and other objects in view that will hereinafter appear, the nature of the invention will be more clearly understood by reference to the following detailed description, the appended claimed subject matter, and the several views illustrated in the accompanying drawing.

IN THE DRAWINGS

By considering an occluding pair of side teeth in front plane it is evident that the protuberances (cusps) and troughs (occlusal reliefs) form a double row shifted at one end. In the normal bite, the lower buccal protuberance of a molar engages into the medial fissure of the upper tooth, and the upper palatinal protuberance engages in the medial fissure of the lower tooth.

Figures 2A, 2B, 2C, 2D, 2E:
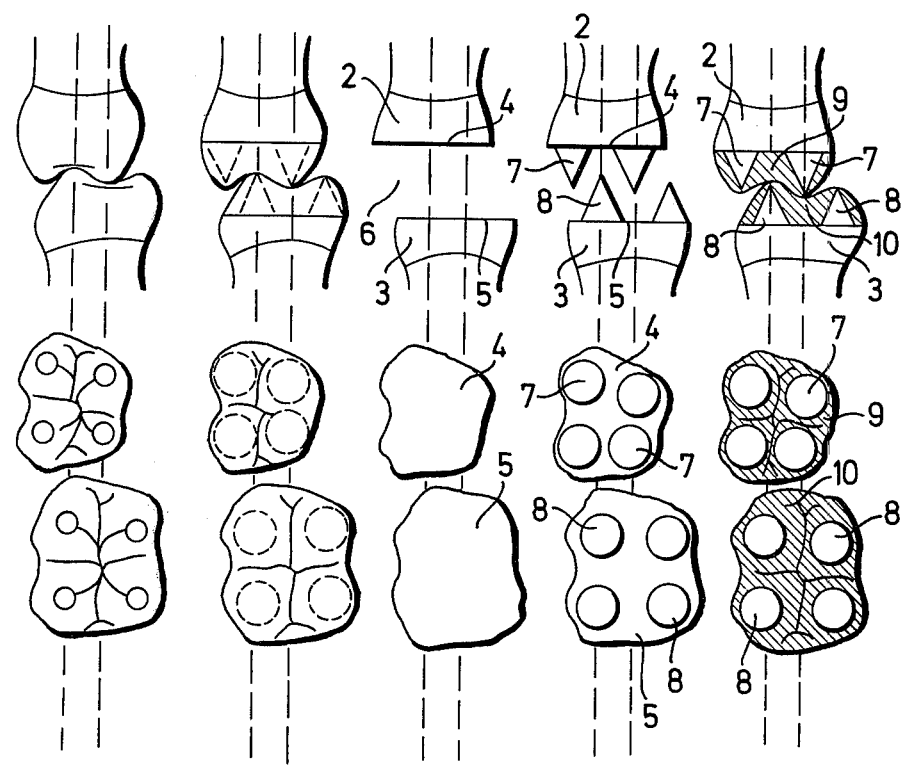
FIGS. 2a–2e illustrate the manner in which base surfaces are prepared, cones adhere thereto, and ceramic material applied.

In manufacturing crowns and bridges, the latter fact must be kept in mind to achieve proper bite and preferably this can be accomplished by the use of an articulator 1 supporting a crown and bridge framework 2,3 provided with a flat uniplanar base surface 4,5 as a mounting area or surface for prefabricated or preformed porcelain base cones 7,8. In order to produce the occlusal relief in such a way that all occlusal patterns come into contact with one another absent undesired disturbance, one proceeds from a normal functional-anatomical occlusion, of which an example is shown in FIG. 2a, both in plan view and front view. Thus, FIG. 2a represents a desired normal molar which can be constructed in a manner shown progressively in FIGS. 2c, 2d, 2e, and 2b, by providing flat uniplanar surfaces 4,5 on the replacement crown and bridge frames 2,3 so that a preparatory occlusal slot 6 results between the cones 7,8 thereof (FIG. 2d). The preformed or prefabricated base cones 7 and/or 8 are adhered to the surfaces 4,5 (FIG. 2d) by an adhesive or by conventional burn-on techniques. This results in an occlusal frame according to FIG. 2d in which the functional surface shape as regards position and distribution of the cones is adapted to an individual's chewing system. Thereafter the occlusal spaces between the cone 7,8 and the surfaces between the base cone 7,8 are filled with ceramic material 9,10 with the completed tooth shape being easily modeled to arrive at the configuration of FIGS. 2e and 2b.

Figure 1:
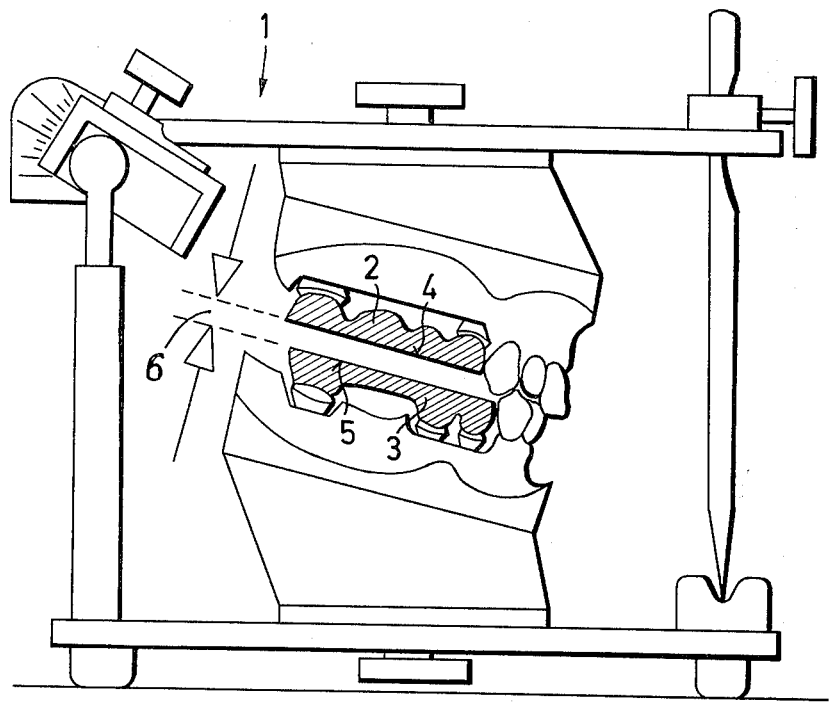
FIG. 1 illustrates schematically a replacement crown and bridge framework, and illustrates opposing base surfaces spaced a predetermined distance from each other prior to adhereing cones thereto.
Figure 3A:
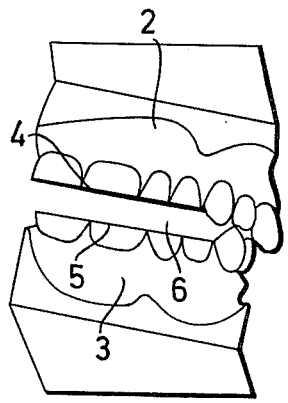
FIGS. 3a–3c are schematic side views, and illustrate progressively the manner in which the cones are positioned between opposing base surfaces in the preparation of the occlusal space within the jaw relationship.
Figure 3B:
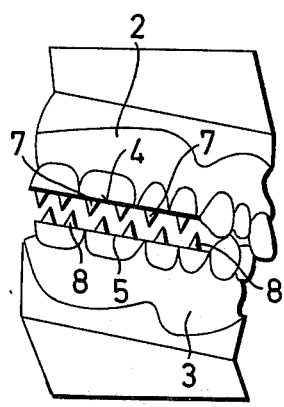
Figure 3C:
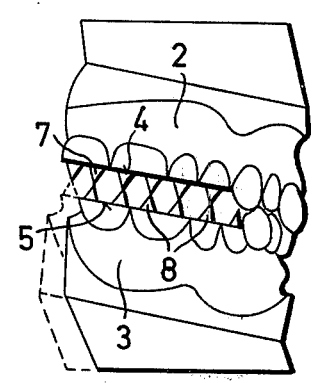

FIGS. 3a–3c show side elevational views of portions of a denture, and in FIG. 3a there is specifically shown an occlusal space 6 between surfaces 4,5 of a replacement crown and bridge framework 2,3. In this case the plane occlusal surfaces 4,5 are parallel to each other and uniplanar, but they also can correspond slightly in curvature to that of the overall chewing system. However, the spacing 6 between the surfaces 4,5 must be uniform and must take into consideration the spacing between existing teeth or replacement teeth, depending upon the nature of the system.

In FIG. 3b the porcelain pre-formed base cones 7,8 are adhered or burned onto the surfaces 4,5, respectively, to result in a symmetrical tooth pattern. The mounting of the base cone 7,8 is appropriately such that the points of the base cones come to bear on one another exactly in the pre-bite phase by half a premolar width, as shown in FIG. 3c. The cones 7,8 are then, of course, covered with ceramic material and modeled to achieve a plurality of molars having cusps or protuberances and occlusal spacings or relief areas therebetween for a proper bite, as indicated in FIGS. 2a, 2b and 2e.

While preferred forms and arrangements of parts have been shown in illustrating the invention, it is to be clearly understood that various changes in detail and arrangement of parts may be made without departing from the spirit and scope of this disclosure.

I claim:

1. A method of manufacturing an artificial molar having cusps and occlusal relief comprising the steps of providing a base surface, providing cones each having a base and apex, securing the base of each cone upon the base surface, and covering the cones with dental material such that cusps are formed by the apices of the cones and occlusal relief is formed between the apices.

2. The method as defined in claim 1 wherein the base surface is planar and flat.

3. The method as defined in claim 1 wherein the cones are of different heights.

4. The method as defined in claim 1 wherein the bases of the cones are of different diameters.

5. The method as defined in claim 1 including the step of providing another base surface, providing additional cones each having a base and apex, securing the base of each additional cone upon the another base surface with the first-mentioned and additional cones being disposed with their apices offset, and covering the additional cones with dental material such that cusps are formed by the apices of the additional cones and occlusal relief is formed between the last-mentioned apices.

6. The method as defined in claim 2 wherein the cones are of different heights.

7. The method as defined in claim 2 wherein the bases of the cones are of different diameters.

8. The method as defined in claim 2 including the step of providing another base surface, providing additional cones each having a base and apex, securing the base of each additional cone upon the another base surface with the first-mentioned and additional cones being disposed with their apices offset, and covering the additional cones with dental material such that cusps are formed by the apices of the additional cones and occlusal relief is formed between the last-mentioned apices.

9. An artificial molar comprising a base surface, a plurality of cones each having a base and apex, means securing each base to said base surface, and dental material means for coating said cones such that cusps are formed by the cone apices and occlusal relief is formed between the apices.

10. The artificial molar as defined in claim 9 wherein said base surface is planar and flat, and said cones are of different heights.

\* \* \* \* \*